(12) United States Patent
Tsuchiya et al.

(10) Patent No.: US 11,284,904 B2
(45) Date of Patent: Mar. 29, 2022

(54) CLIP TREATMENT TOOL (71) Applicant: FUJIFILM Corporation, Tokyo (JP)

(72) Inventors: Syuji Tsuchiya, Kanagawa (JP); Koji Itoh, Kanagawa (JP); Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 318 days.

(21) Appl. No.: 16/699,718

(22) Filed: Dec. 1, 2019

(65) Prior Publication Data

US 2020/0100791 A1 Apr. 2, 2020

Related U.S. Application Data (63) Continuation of application No. PCT/JP2018/015159, filed on Apr. 11, 2018.

(30) Foreign Application Priority Data

Jun. 21, 2017 (JP) .............................. JP2017-121184

(51) Int. Cl.
*A61B 17/122* (2006.01)
*A61B 17/128* (2006.01)
*A61B 17/12* (2006.01)

(52) U.S. Cl.
CPC ........ *A61B 17/122* (2013.01); *A61B 17/1285* (2013.01); *A61B 2017/12004* (2013.01)

(58) Field of Classification Search
None
See application file for complete search history.

(56) References Cited

U.S. PATENT DOCUMENTS 7,452,327 B2  11/2008 Durgin et al.
8,083,668 B2  12/2011 Durgin et al.
(Continued)

FOREIGN PATENT DOCUMENTS

CN  105935304  9/2016
JP  2008289524  12/2008
(Continued)

OTHER PUBLICATIONS

"Search Report of Europe Counterpart Application", dated Jun. 3, 2020, pp. 1-10.

(Continued)

*Primary Examiner* — Shaun L David
(74) *Attorney, Agent, or Firm* — JCIPRNET (57) ABSTRACT

A clip treatment tool includes a clip body that has two clip-pieces, the two clip-pieces each having a body-portion and an arm-portion, the body-portion having a fixing-hole formed on a proximal end side and a movement hole formed on a distal end side relative to the fixing-hole, the movement hole extending so as to be inclined from a side part in a width direction of the body-portion on the proximal end side toward a middle in the width direction of the body-portion on the distal end side; a container tube that contains the body-portions of the two clip-pieces therein; a stopper that extends through the fixing-holes of the two clip-pieces and that is attached to the clip body; and a fixing pin that extends through the movement holes of the two clip-pieces and whose both end portions are fixed to positions in the container tube that face each other.

8 Claims, 7 Drawing Sheets

(56) References Cited

U.S. PATENT DOCUMENTS

| | | | |
|---|---|---|---|
| 8,974,371 | B2 | 3/2015 | Durgin et al. |
| 9,339,270 | B2 | 5/2016 | Martinez et al. |
| 9,370,371 | B2 | 6/2016 | Durgin et al. |
| 9,795,390 | B2 | 10/2017 | Jin et al. |
| 9,949,740 | B2 | 4/2018 | Satake et al. |
| 9,980,725 | B2 | 5/2018 | Durgin et al. |
| 2004/0044363 | A1* | 3/2004 | Fowler ............... A61B 17/1285 606/205 |
| 2012/0065646 | A1 | 3/2012 | Phillips-Hungerford et al. |
| 2014/0171973 | A1 | 6/2014 | Zhu |
| 2016/0220261 | A1 | 8/2016 | Menn et al. |
| 2016/0367258 | A1* | 12/2016 | Jin ..................... A61B 17/1285 |
| 2018/0193022 | A1 | 7/2018 | Satake et al. |
| 2018/0235608 | A1 | 8/2018 | Durgin et al. |

FOREIGN PATENT DOCUMENTS

| | | |
|---|---|---|
| JP | 4921173 | 4/2012 |
| JP | 5750619 | 7/2015 |
| JP | 2017509392 | 4/2017 |

OTHER PUBLICATIONS

"International Search Report (Form PCT/ISA/210) of PCT/JP2018/015159", dated Jun. 26, 2018, with English translation thereof, pp. 1-5.

"Written Opinion of The International Searching Authority (Form PCT/ISA/237) of PCT/JP2018/015159", dated Jun. 26, 2018, with English translation thereof, pp. 1-9.

\* cited by examiner

CLIP TREATMENT TOOL

CROSS-REFERENCE TO RELATED APPLICATIONS

This application is a Continuation of PCT International Application No. PCT/JP2018/015159 filed on Apr. 11, 2018, which claims priority under 35 U.S.C. § 119(a) to Japanese Patent Application No. 2017-121184 filed on Jun. 21, 2017. Each of the above application(s) is hereby expressly incorporated by reference, in its entirety, into the present application.

BACKGROUND OF THE INVENTION

1. Field of the Invention

The present invention relates to a clip treatment tool for an endoscope, which is used, for example, to close a wound and to stop bleeding in a living body.

2. Description of the Related Art

A clip treatment tool for an endoscope is used, for example, to close a wound and to stop bleeding by extruding arm portions of a clip from a distal end of the endoscope, which is inserted into a living body, and by ligating a treatment part, such as the wound and the bleeding part, with distal end parts of the arm portions of the clip.

Examples of such a clip treatment tool known to date include clip treatment tools that can freely open and close arm portions of a clip, as described in JP5750619B, JP4921173B, U.S. Pat. No. 9,339,270B, US2016/0367258A, and JP2008-289524A. By using the known technologies described in these patent documents, for example, it is possible to freely open and close arm portions of a clip in the body of a patient to hold a treatment part over again, and therefore it is possible to apply the clip to an accurate position on the treatment part and to perform treatment such as stoppage of bleeding.

SUMMARY OF THE INVENTION

However, once the treatment part has been ligated by the clip, the clip is placed in the body of the patient. Therefore, when the clip is placed in the body at a position displaced from a target position to be ligated due to an erroneous operation or the like, and when, for example, the clip placed in the body becomes unnecessary after bleeding or the like has been sufficiently stopped, the clip remains placed in the living body, and it is necessary to wait until the clip is naturally removed due to a change in body tissue of the patient. That is, there is a problem in that it is not possible to remove the clip at a desirable timing.

An object of the present invention is to provide a clip treatment tool with which, after the clip has been once applied, it is possible to reliably maintain the applied state, and it is possible to remove a clip placed in a living body at any desirable timing.

In order to achieve the object, the present invention provides a clip treatment tool including: a clip body that has two clip pieces, each of the two clip pieces having a body portion and an arm portion, the arm portions of the two clip pieces facing each other and respectively extending from the body portions toward a distal end side, each of the body portions of the two clip pieces having a fixing hole formed on a proximal end side and a movement hole formed on the distal end side relative to the fixing hole, the movement hole extending so as to be inclined from a side part in a width direction of the body portion on the proximal end side toward a middle in the width direction of the body portion on the distal end side; a container tube that contains the body portions of the two clip pieces therein; a stopper that extends through the fixing holes of the two clip pieces and that is attached to the clip body; and a fixing pin that extends through the movement holes of the two clip pieces and whose both end portions are fixed to positions in the container tube that face each other. The arm portions of the two clip pieces open in accordance with movement of the clip body from the proximal end side toward the distal end side, and the arm portions of the two clip pieces close in accordance with movement of the clip body from the distal end side toward the proximal end side.

Preferably, the movement hole of each of the two clip pieces has a proximal-end-side region and a distal-end-side region, the proximal-end-side region extending so as to be inclined from the side part in the width direction of the body portion on the proximal end side toward the middle in the width direction of the body portion on the distal end side, the distal-end-side region being located at the middle in the width direction of the body portion on the distal end side and extending from the proximal-end-side region toward the distal end side; and the body portions of the two clip pieces move in such a way that a position of the fixing pin moves along the proximal-end-side regions of the movement holes of the two clip pieces relatively from the distal end side toward the proximal end side, and the arm portions of the two clip pieces open; and the body portions of the two clip pieces move in such a way that the position of the fixing pin moves along the proximal-end-side regions of the movement holes of the two clip pieces relatively from the proximal end side toward the distal end side, and the arm portions of the two clip pieces close.

Preferably, the position of the fixing pin relatively moves from the proximal-end-side regions to the distal-end-side regions of the movement holes of the two clip pieces, and the arm portions of the two clip pieces enter a closed state.

Preferably, an opening is formed in the container tube; and, in accordance with movement of the clip body from the distal end side toward the proximal end side, the stopper moves to a position of the opening and is fitted into the opening, and the clip body is locked to the container tube.

Preferably, the position of the fixing pin relatively moves to most distal end parts of the distal-end-side regions of the movement holes of the two clip pieces, and the clip body is locked to the container tube while the arm portions of the two clip pieces are in the closed state.

Preferably, the clip treatment tool includes a coupling member that has a latch portion on the distal end side, the latch portion being removably latched to proximal end sides of the body portions of the two clip pieces of the clip body and a distal end part of an operation wire being fixed to a proximal end side of the coupling member, the coupling member coupling the clip body and the operation wire to each other; each of the two clip pieces has a coupling hole that is formed in the body portion on the proximal end side of the fixing hole, that extends in the width direction of the body portion, and that is latched by the latch portion, and the coupling hole has a passage opening that is open toward the proximal end side; the arm portions of the two clip pieces gradually close from an open state, overlap between the passage openings of the coupling holes of the two clip pieces gradually increases, and an opening diameter of the passage openings increases; and, while the arm portions of the two clip pieces are in the closed state, the clip body is locked to the container tube, the opening diameter of the passage openings of the coupling holes of the two clip pieces becomes maximum, and, in accordance with movement of the coupling member from the distal end side toward the proximal end side, the latch portion is removed through the passage openings, the two clip pieces and the coupling member are unlatched from each other, and the clip body and the operation wire are separated from each other.

Preferably, the clip treatment tool includes a container tube holder that has a tubular shape and that has a holding portion on the distal end side; the holding portion has two or more holding members that are disposed so as to face each other, and the two or more holding members respectively have extending portions that extend so as to become closer to each other from the proximal end side toward the distal end side and claw portions that extend so as to become farther from each other from distal end parts of the extending portions toward the distal end side; a recessed portion is formed in an inner peripheral surface on the proximal end side of the container tube; the coupling member has a coupling member body between the latch portion and the operation wire, the coupling member body having an outside diameter larger than an inside diameter of the two or more holding members at a position between the extending portions and the claw portions, the coupling member body is inserted through a space between the two or more holding members, the extending portions of the two or more holding members are pushed and expanded by the coupling member body so as to become farther from each other, the claw portions the two or more holding members are latched to the recessed portion of the container tube, and the container tube is removably attached to a distal end part of the container tube holder; and, in accordance with movement of the coupling member from the distal end side toward the proximal end side, a distal end part of the coupling member body moves to a position on the proximal end side relative to the position between the extending portions and the claw portions of the two or more holding members, the extending portions move closer to each other due to an elastic force, the claw portions of the two or more holding members and the recessed portion of the container tube are disengaged from each other, and the container tube and the container tube holder are separated from each other.

Preferably, in a state in which the container tube and the container tube holder are separated from each other, outer surfaces of the stopper are pressed, the stopper and the opening are released from each other, the clip body and the container tube are unlocked, and, in accordance with movement of the clip body from the proximal end side toward the distal end side, the arm portions of the two clip pieces gradually open from the closed state and enter the open state.

With the present invention, until a treatment part is ligated by a clip unit, which is composed of the clip body, the container tube, the stopper, and the fixing pin, it is possible to hold the treatment part over again by using the two clip pieces; and, after the treatment part has been ligated by the clip unit, because the clip body and the container tube are locked, it is possible to reliably maintain the state in which the treatment part is ligated by the clip unit. Moreover, after the clip unit is placed at the treatment part, it is possible to remove the clip unit from the treatment part by unlocking the clip body and the container tube at any desirable timing.

DESCRIPTION OF THE PREFERRED EMBODIMENTS

Hereafter, a clip treatment tool according to the present invention will be described in detail based on preferred embodiments illustrated in the drawings.

Figure 1:
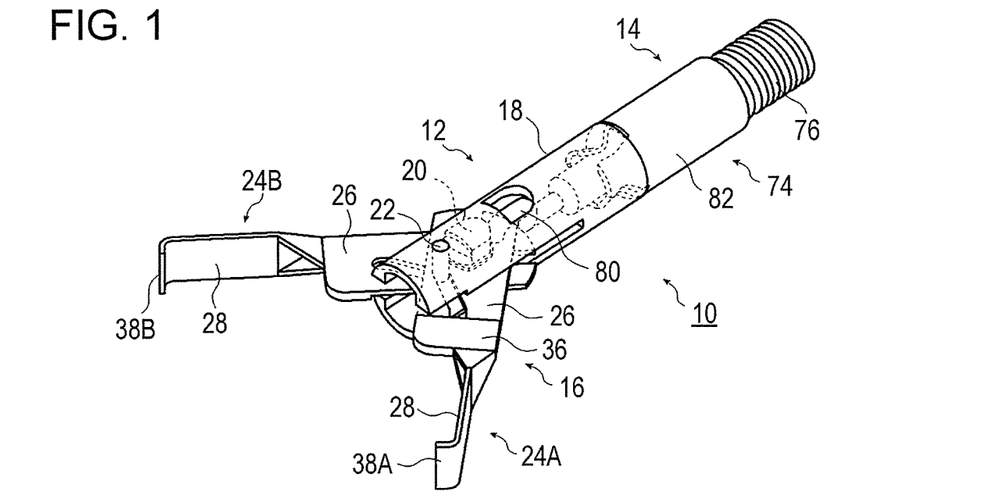
FIG. 1 is a partially see-through external perspective view of a clip treatment tool according to an embodiment of the present invention.
Figure 2:
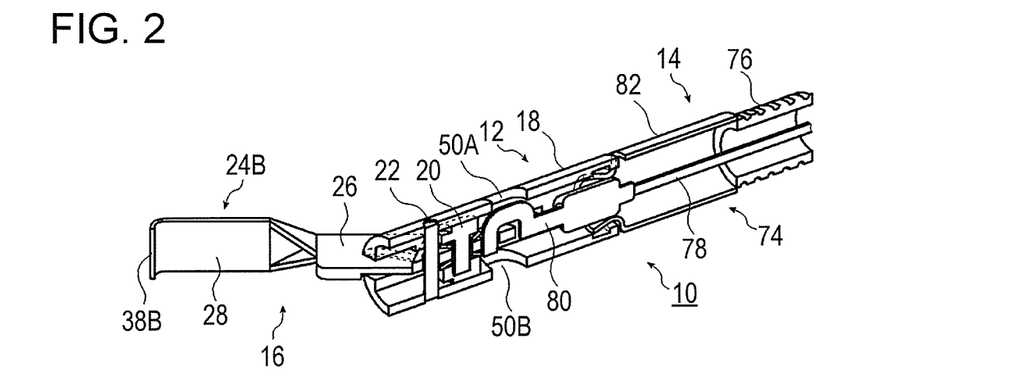
FIG. 2 is a partially sectional perspective view of the clip treatment tool illustrated in FIG. 1.

FIG. 1 is a partially see-through external perspective view of a clip treatment tool according to an embodiment of the present invention. FIG. 2 is a partially sectional perspective view of the clip treatment tool illustrated in FIG. 1.

Figure 9:
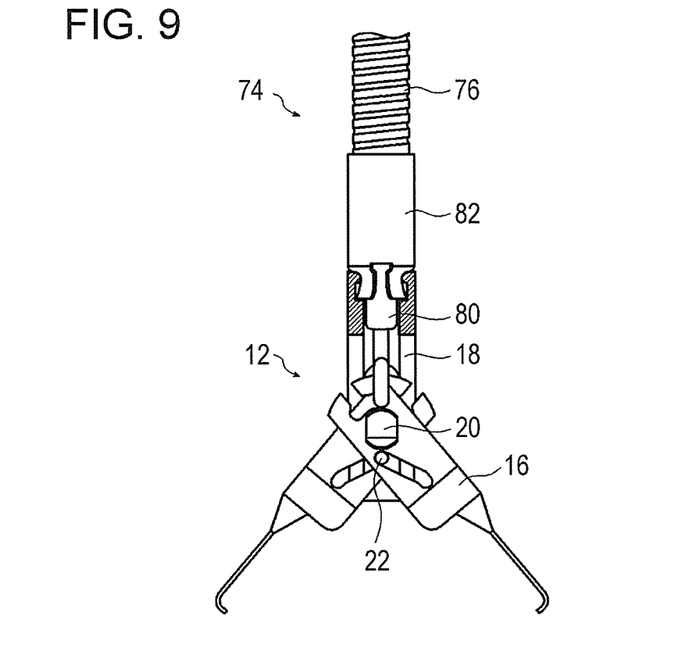
FIG. 9 is an external partial side view of the clip treatment tool according to the present invention, in a state in which arm portions of two clip pieces are in an open state.

In the present embodiment, a first direction is defined as the direction in which arm portions of two clip pieces face each other (direction perpendicular to the plane of FIG. 13A), and a second direction is defined as the direction perpendicular to both of the first direction and the axial direction of a container tube (direction perpendicular to the plane of FIG. 9). In the clip treatment tool, a side on which a treatment part is located is defined as the distal end side, and a side on which an operator is located is defined as the proximal end side.

In all figures, in order to facilitate understanding, the dimensions, such as the thickness and the length, of each element of the present embodiment are appropriately changed from the actual dimensions, as necessary.

A clip treatment tool 10 illustrated in FIGS. 1 and 2 includes a clip unit 12 and a treatment tool body 14. When operated by an operator, for example, the clip treatment tool 10 is inserted from a treatment tool inlet of an operation portion of an endoscope, is extruded from a treatment tool outlet of a distal end surface of an insertion portion of the endoscope that has been inserted into the body of a patient, and ligates a treatment part by using the clip unit 12.

The clip unit 12 includes a clip body 16, a container tube 18, a stopper 20, and a fixing pin 22.

The clip body 16 has two clip pieces, which are a first clip piece 24A and a second clip piece 24B.

Figure 3:
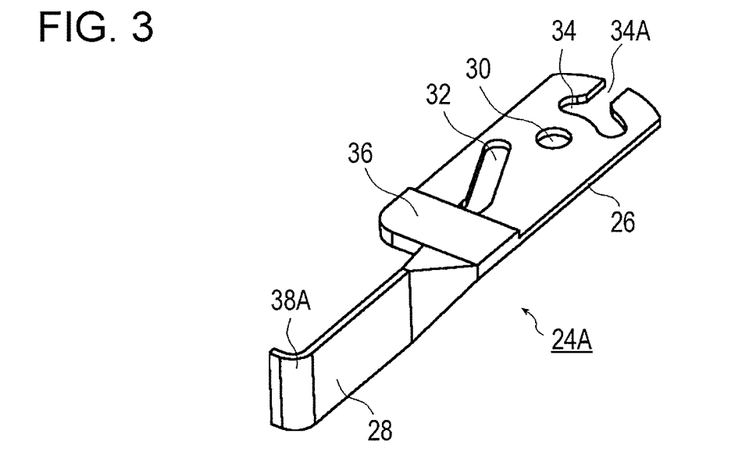
FIG. 3 is an external perspective view of a first clip piece according to the embodiment.

FIG. 3 is an external perspective view of the first clip piece according to an embodiment. As illustrated in FIG. 3, the first clip piece 24A has a body portion 26 and an arm portion 28.

The body portion 26 has a flat plate-like shape. In the body portion 26, a fixing hole 30, a movement hole 32, and a coupling hole 34 are formed.

The fixing hole 30 has a circular shape and is formed on the proximal end side of the body portion 26 at a middle part in the width direction of the body portion 26 (a direction perpendicular to the second direction and the extension direction of the arm portion 28).

The movement hole 32 is formed in the body portion 26 on the distal end side relative to the fixing hole 30. The movement hole 32 extends so as to be inclined from a side part in the width direction on one side of the body portion 26 on the proximal end side toward the middle in the width direction of the body portion 26 on the distal end side. To be more specific, the movement hole 32 has a proximal-end-side region and a distal-end-side region. The proximal-end-side region has a curved or linear shape and extends so as to be inclined at a constant angle from the one side part in the width direction of the body portion 26 on the proximal end side toward the middle in the width direction of the body portion 26 on the distal end side. The distal-end-side region has a linear shape, is located at the middle of the body portion 26 on the distal end side, and extends from the proximal-end-side region toward the distal end side.

The coupling hole 34 is formed in the body portion 26 on the proximal end side of the fixing hole 30 so as to extend in the width direction of the body portion 26. To be more specific, the coupling hole 34 extends in the width direction of the body portion 26 so as to be curved at a constant angle to form an arc that is centered on the fixing hole 30. The coupling hole 34 has a passage opening 34A that is open toward the proximal end side. The passage opening 34A is formed by cutting off a part of the body portion 26 from the coupling hole 34 toward the proximal end side at a middle part of the body portion 26 in the width direction.

A base portion 36 for disposing the arm portion 28 is formed on the distal end side of one surface of the body portion 26. The base portion 36 has a thickness that is larger than the thickness of parts of the body portion 26 other than the base portion 36 so that the arm portion 28 can be easily disposed on the body portion 26.

The arm portion 28 extends from the body portion 26 toward the distal end side. To be more specific, the arm portion 28 extends from the other side of a distal end part of the base portion 36 toward the distal end side. The arm portion 28 has a first claw portion 38A that is formed at a distal end part of the arm portion 28. The first claw portion 38A is formed by bending the distal end part of the arm portion 28 at a constant angle toward one side in the width direction of the body portion 26.

The second clip piece 24B is configured similarly to the first clip piece 24A. In the body portion 26 of the second clip piece 24B, a fixing hole 30, a movement hole 32, a coupling hole 34, and a base portion 36 are formed at positions respectively corresponding to the fixing hole 30, the movement hole 32, and the coupling hole 34, and the base portion 36 of the first clip piece 24A. At a distal end part of the arm portion 28 of the second clip piece 24B, a second claw portion 38B is formed at a position corresponding to the first claw portion 38A of the first clip piece 24A. The first claw portion 38A and the second claw portion 38B are portions for holding a treatment part therebetween and ligating the treatment part.

The two clip pieces 24A and 24B are disposed in such a way the other surfaces of the body portions 26, that is, flat surfaces on which the base portions 36 are not formed are superposed on each other with the fixing holes 30 at the center. Thus, the arm portions 28 of the two clip pieces 24A and 24B are disposed so as to face each other, so as to respectively extend from the body portions 26 toward the distal end side, and so that the first claw portion 38A and the second claw portion 38B of the two clip pieces 24A and 24B face each other.

Figure 4:
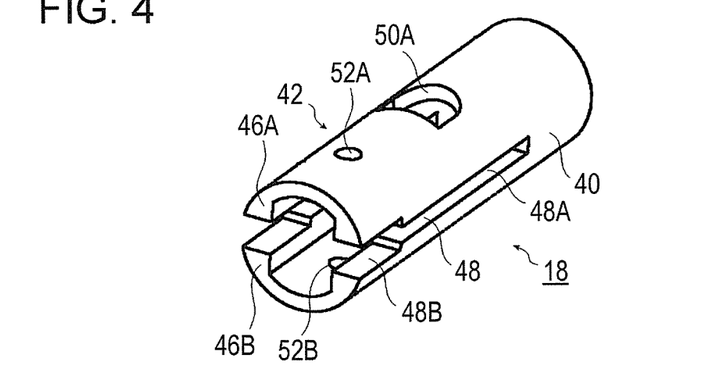
FIG. 4 is an external perspective view of a container tube according to the embodiment.

FIG. 4 is an external perspective view of the container tube according to the embodiment. As illustrated in FIG. 4, the container tube 18 has a container tube body 40 and a containing portion 42.

A recessed portion 44 (see FIG. 11) is formed in an inner peripheral surface on the proximal end side of the container tube 18, that is, the proximal end side of the container tube body 40 along the entire periphery.

The containing portion 42 is disposed on the distal end side from the container tube body 40, and the container tube body 40 and the containing portion 42 are integrally formed. The containing portion 42 has a first containing member 46A and a second containing member 46B.

The first containing member 46A and the second containing member 46B extend parallelly from the container tube body 40 toward the distal end side so as to face each other. The first containing member 46A and the second containing member 46B are disposed with a constant distance therebetween in the second direction. That is, holes 48, which extend in the axial direction, are formed in both side surfaces of the container tube 18. Each of the holes 48 has a first hole 48A on the proximal end side and a second hole 48B on the distal end side. The size of the first hole 48A in the second direction is slightly larger than the thickness of parts of the two clip pieces 24A and 24B other than the base portions 36 when the parts are superposed on each other. The size of the second hole 48B in the second direction is slightly larger than the thickness of the base portions 36 of the two clip pieces 24A and 24B when the base portions 36 are superposed on each other.

A first opening 50A and a second opening 50B (see FIG. 2), which have substantial D-shapes, are formed at positions in both side surfaces in the second direction of the first containing member 46A and the second containing member 46B of the container tube 18 on the proximal end side. Substantially D-shaped curved portions of the first opening 50A and the second opening 50B are oriented toward the proximal end side. A first insertion hole 52A and a second insertion hole 52B, which are circular, are formed in the side surfaces in the second direction of the first containing member 46A and the second containing member 46B on the distal end side.

In accordance with movement of the clip body 16 from the proximal end side toward the distal end side, the container tube 18 functions to expose the body portions 26 of the two clip pieces 24A and 24B from the inside thereof through the holes 48 in both side surfaces; and, in accordance with movement of the clip body 16 from the distal end side toward the proximal end side, the container tube 18 functions to allow the body portions 26 of the two clip pieces 24A and 24B to be contained therein through the holes 48 in both side surfaces.

Figure 5A:
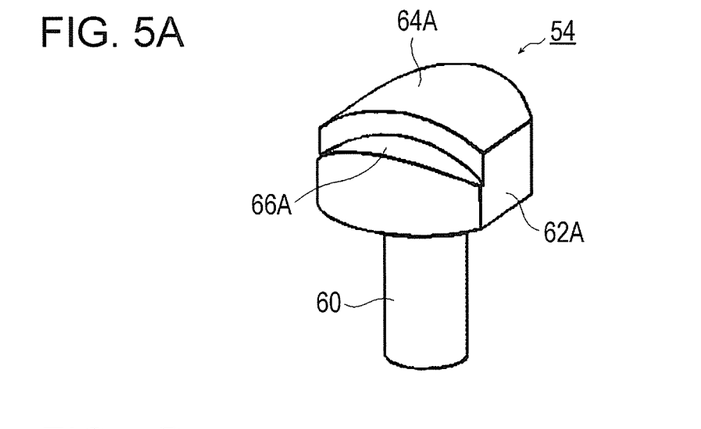
FIG. 5A is an external perspective view of a first stopper member of a stopper according to the embodiment.
Figure 5B:
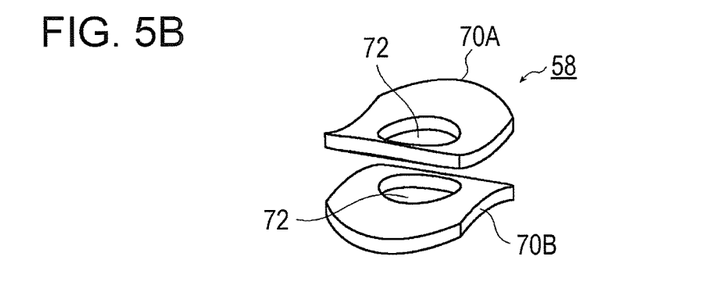
FIG. 5B is an external perspective view of an urging member of the stopper according to the embodiment.
Figure 5C:
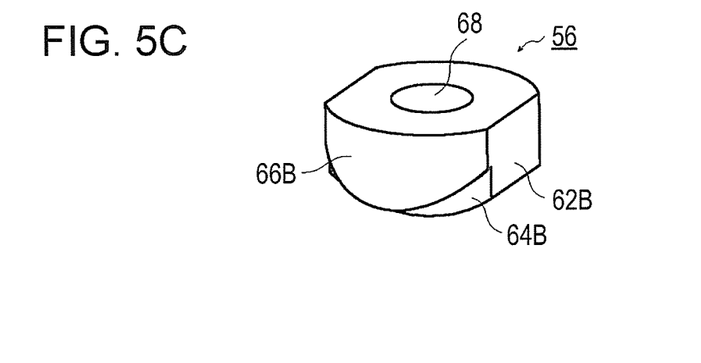
FIG. 5C is an external perspective view of a second stopper member of the stopper according to the embodiment.

FIGS. 5A, 5B, and 5C are respectively external perspective views of a first stopper member, an urging member, and a second stopper member of the stopper according to the embodiment. As illustrated in FIGS. 5A, 5B, and 5C, the stopper 20 has a first stopper member 54, a second stopper member 56, and an urging member 58.

The first stopper member 54 has a through pin 60 and a first fitting portion 62A.

The through pin 60 is bar-shaped and is inserted through the fixing holes 30 of the two clip pieces 24A and 24B.

The first fitting portion 62A is formed on at one end part of the through pin 60. The shape of an outer surface of the first fitting portion 62A as seen in the second direction is an elliptical shape extending in the axial direction of the container tube 18. The first fitting portion 62A has a first fitting member 64A and a second fitting member 66A, and the first fitting member 64A and the second fitting member 66A are integrally formed. The height of the first fitting member 64A in the second direction is larger than the height of the second fitting member 66A in the second direction. The shape of the outer surface of the first fitting member 64A as seen in the second direction is a substantial D-shape, which is the same as the shape of the first opening 50A of the container tube 18 as seen in the second direction. The first fitting member 64A has a size such that the first fitting member 64A can be fitted into the first opening 50A of the container tube 18.

The second stopper member 56 has a second fitting portion 62B, which has a shape similar to the first fitting portion 62A of the first stopper member 54. That is, the second fitting portion 62B has a first fitting member 64B and a second fitting member 66B, which correspond to the first fitting member 64A and the second fitting member 66A of the first fitting portion 62A. The second fitting portion 62B has a recessed portion 68 that is formed in a middle part of the inner surface thereof facing the first stopper member 54. The inside diameter of the recessed portion 68 of the second stopper member 56 is slightly larger than the diameter of the through pin 60 of the first stopper member 54.

The first opening 50A and the second opening 50B of the container tube 18 are formed at positions in both side surfaces of the container tube 18 that respectively correspond to the first fitting portion 62A and the second fitting portion 62B in a state in which the clip body 16 is locked to the container tube 18.

The urging member 58 is disposed between the first stopper member 54 and the second stopper member 56 and urges the first stopper member 54 and the second stopper member 56 in directions away from each other. In the present embodiment, the urging member 58 has two plate springs 70A and 70B. As seen in the second direction, the two plate springs 70A and 70B have elliptical shapes and outside diameters that are substantially the same as the shapes and outside diameters of the first fitting portion 62A and the second fitting portion 62B as seen in the second direction. In middle parts of the two plate springs 70A and 70B, through-holes 72, through which the through pin 60 of the first stopper member 54 is inserted, are formed. The two plate springs 70A and 70B are bent with a constant curvature at middle parts thereof in the extension direction of the elliptical shapes. The two plate springs 70A and 70B are superposed on each other so that convex surfaces thereof face each other and are disposed between the first stopper member 54 and the second stopper member 56.

The through pin 60 of the first stopper member 54 is inserted through the through-hole 72 of the plate spring 70A, the fixing holes 30 of the two clip pieces 24A and 24B, and the through-hole 72 of the plate spring 70B in this order. The other end part of the through pin 60 is inserted into the recessed portion 68 of the second fitting portion 62B of the second stopper member 56 in such a way that the first stopper member 54 and the second stopper member 56 are movable in the axial direction of the through pin 60.

In a state before the clip body 16 is locked to the container tube 18, the stopper 20 is urged in the container tube 18 by the two plate springs 70A and 70B in directions away from each other, and both end parts of the first stopper member 54 and the second stopper member 56 are in contact with parts of the inner peripheral surfaces of the container tube 18 facing each other. Thus, the stopper 20 extends through the fixing holes 30 of the two clip pieces 24A and 24B and is attached to the clip body 16.

Figure 6:
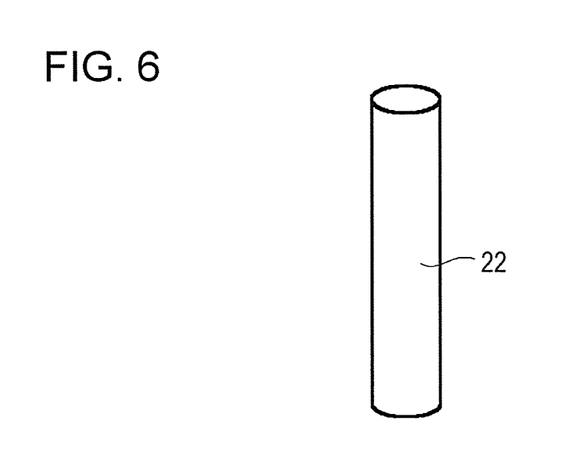
FIG. 6 is an external perspective view of a fixing pin according to the embodiment.

FIG. 6 is an external perspective view of the fixing pin according to the embodiment.

The fixing pin 22 is bar-shaped as illustrated in FIG. 6, and is inserted through the movement holes 32 of the two clip pieces 24A and 24B. Both end portions of the fixing pin 22 are inserted through the first insertion hole 52A of the first containing member 46A and the second insertion hole 52B of the second containing member 46B of the container tube 18, and are fixed to positions in the inner peripheral surface of the container tube 18 facing each other.

In accordance with movement of the clip body 16 from the proximal end side toward the distal end side, the body portions 26 of the two clip pieces 24A and 24B move so that the positions where the movement holes 32 of the body portions 26 of the two clip pieces 24A and 24B are in contact with the fixing pin 22 move along the proximal-end-side regions from the distal end side toward the proximal end side, the body portions 26 are exposed from the holes 48 of both side surfaces the container tube 18, and the arm portions 28 of the two clip pieces 24A and 24B open. In accordance with movement of the clip body 16 from the distal end side toward the proximal end side, the body portions 26 of the two clip pieces 24A and 24B move so that the positions where the movement holes 32 of the body portions 26 of the two clip pieces 24A and 24B are in contact with the fixing pin 22 move along the proximal-end-side regions from the proximal end side toward the distal end side, the body portions 26 are contained in the container tube 18 from the holes 48 of both side surfaces the container tube 18, and the arm portions 28 of the two clip pieces 24A and 24B close.

The clip body 16, the container tube 18, the stopper 20, and the fixing pin 22 of the clip unit 12 are made of a material such as a stainless steel, titanium, or a cobalt-chrome alloy. Accordingly, even after the clip unit 12 is placed in the body of a patient, the patient can have a magnetic resonance imaging (MRI) scan.

The treatment tool body 14 includes an insertion portion 74 and an operation portion (not shown).

The insertion portion 74 includes a coil sheath 76, an operation wire 78, a coupling member 80, and a container tube holder 82 that is tubular.

The coil sheath 76 is a flexible tube that is made of, for example, a fluorocarbon resin such as polytetrafluoroethylene (PTFE) or a resin material such as high-density polyethylene (HDPE).

The operation wire 78 is made from, for example, a single wire or a stranded wire made of a metal. The operation wire 78 is inserted through the inside of the coil sheath 76 so as to be movable in the axial direction of the coil sheath 76, and further extends from both end portions of the coil sheath 76 toward the distal end side and the proximal end side. The diameter of the operation wire 78 is slightly larger than the maximum opening diameter of the passage openings 34A of the coupling holes 34 of the two clip pieces 24A and 24B when the passage openings 34A completely overlap.

When an operator operates the operation portion of the treatment tool body 14, the operation wire 78 moves in the coil sheath 76 toward the distal end side or the proximal end side. That is, the operator can push the operation wire 78 from the proximal end side toward the distal end side or pull the operation wire 78 from the distal end side toward the proximal end side.

Figure 7:
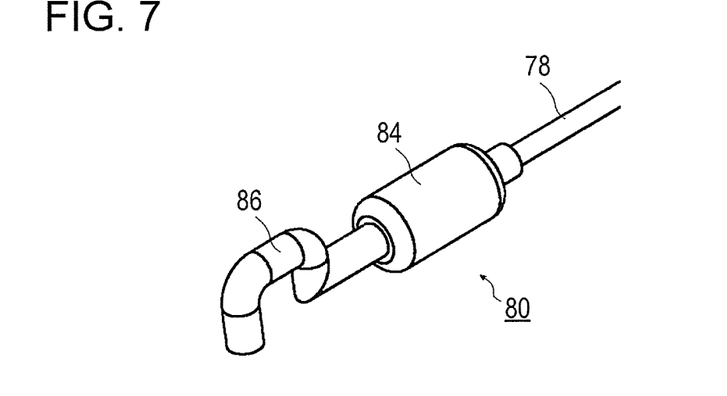
FIG. 7 is an external perspective view of a coupling member according to the embodiment.

FIG. 7 is an external perspective view of the coupling member according to the embodiment.

The coupling member 80 has a coupling member body 84 and a latch portion 86 as illustrated in FIG. 7, and is made of, for example, a biocompatible resin. In the state before the clip body 16 is locked to the container tube 18, the coupling member 80 is contained in the container tube 18.

The coupling member body 84 is cylindrical, and a distal end part of the operation wire 78 is fixed to a proximal end part of the coupling member body 84. That is, the coupling member body 84 is disposed between the latch portion 86 and the operation wire 78. The outside diameter of the coupling member body 84 is smaller than the inside diameter of the container tube 18.

The latch portion 86 has a distal end part that is hook-shaped and extends from the coupling member body 84 toward the distal end side. The coupling member body 84 and the latch portion 86 are integrally formed.

The hook-shaped distal end part of the latch portion 86 is inserted into the coupling holes 34 of the body portions 26 of the two clip pieces 24A and 24B, the coupling holes 34 of the two clip pieces 24A and 24B are latched by the latch portion 86, and the latch portion 86 is removably latched to the clip body 16.

Thus, the latch portion 86 is removably latched to the proximal end sides of the body portions 26 of the two clip pieces 24A and 24B of the clip body 16, the distal end part of the operation wire 78 is fixed to the proximal end side of the coupling member 80, and the clip body 16 and the operation wire 78 are coupled to each other by the coupling member 80.

In accordance with movement of the operation wire 78 from the proximal end side toward the distal end side, the coupling member 80 moves from the proximal end side toward the distal end side; and, in accordance with movement of the coupling member 80 from the proximal end side toward the distal end side, the clip body 16 moves from the proximal end side toward the distal end side. In accordance with movement of the operation wire 78 from the distal end side toward the proximal end side, the coupling member 80 moves from the distal end side toward the proximal end side; and, in accordance with movement of the coupling member 80 from the distal end side toward the proximal end side, the clip body 16 moves from the distal end side toward the proximal end side.

Figure 8:
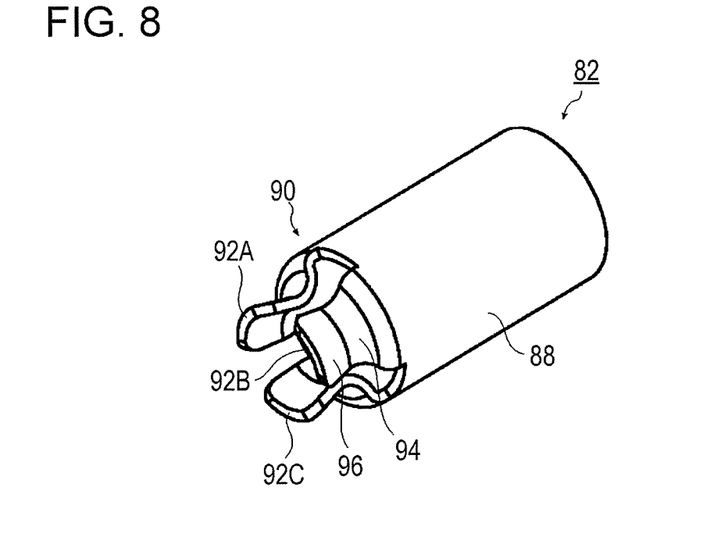
FIG. 8 is an external perspective view of a container tube holder according to the embodiment.

FIG. 8 is an external perspective view of the container tube holder according to the embodiment.

As illustrated in FIG. 8, the container tube holder 82 has a holder body 88 having a tubular shape and a holding portion 90 that holds the container tube 18.

The holding portion 90 is disposed on the distal end side of the holder body 88 and has two or more holding members, which are three holding members 92A, 92B, and 92C in the present embodiment. The three holding members 92A, 92B, and 92C are disposed so as to face each other and extend from the holder body 88 toward the distal end side. The three holding members 92A, 92B, and 92C respectively have extending portions 94 that extend so as to become closer to each other from the proximal end side toward the distal end side and claw portions 96 that extend so as to become farther from each other from distal end parts of the extending portions 94.

The inside diameter of the three holding members 92A, 92B, and 92C at a position between the extending portions 94 and the claw portions 96 is smaller than the outside diameter the coupling member body 84 of the coupling member 80 in a state in which an external force is not applied to the three holding members 92A, 92B, and 92C. That is, in the state in which an external force is not applied to the three holding members 92A, 92B, and 92C, the coupling member body 84 has an outside diameter that is larger than the inside diameter of the three holding members 92A, 92B, and 92C at a position between the extending portions 94 and the claw portions 96. The inside diameter of the container tube holder 82 is larger than the outside diameter of the coupling member body 84.

In the state before the clip body 16 is locked to the container tube 18, the coupling member body 84 is inserted through the space among the three holding members 92A, 92B, and 92C, the extending portions 94 of the three holding members 92A, 92B, and 92C are pushed and expanded by the coupling member body 84 so as to become farther from each other, and the claw portions 96 of the three holding members 92A, 92B, and 92C are latched to the recessed portion 44 of the container tube body 40. Thus, the container tube 18 is removably attached to a distal end part of the container tube holder 82.

The operation portion of the treatment tool body 14 has an operation portion body, a slider, and the like (not shown).

A distal end part of the operation portion body is attached to a proximal end part of the coil sheath 76.

The slider is a portion that moves the operation wire 78 toward the distal end side or the proximal end side relative to the coil sheath 76. The slider is slidable relative to the operation portion body toward the distal end side or the proximal end side. A proximal end part of the operation wire 78 is fixed to a distal end part of the slider.

When an operator operates the operation portion of the treatment tool body 14 and the slider is moved relative to the operation portion body from the proximal end side toward the distal end side, the operation wire 78 is moved from the proximal end side toward the distal end side. When the slider moves relative to the operation portion body from the distal end side toward the proximal end side, the operation wire 78 is moved from the distal end side toward the distal end side.

Next, actions of the clip treatment tool 10 will be described.

First, an action that is performed when ligating a treatment part by using the clip unit 12 will be described. In the following description, it is assumed that an insertion portion of an endoscope (not shown) has already been inserted into the body of a patient.

First, when operated by an operator, the insertion portion 74 of the clip treatment tool 10 is inserted from a treatment tool inlet of the endoscope (not shown), and a distal end part of the insertion portion 74 of the clip treatment tool 10, to be more specific, a distal end part of the clip unit 12 is extruded from a treatment tool outlet of the endoscope.

Next, when the operator operates the operation portion of the treatment tool body 14, the operation wire 78 is moved from the proximal end side toward the distal end side.

In accordance with movement of the operation wire 78 from the proximal end side toward the distal end side, the coupling member 80 and the clip body 16 move from the proximal end side toward the distal end side. In accordance with movement of the clip body 16 from the proximal end side toward the distal end side, the body portions 26 of the two clip pieces 24A and 24B move in such a way that the position of the fixing pin 22 moves along the proximal-end side regions of the movement holes 32 of the two clip pieces 24A and 24B relatively from the distal end side toward the proximal end side, and the arm portions 28 of the two clip pieces 24A and 24B of the clip body 16 enter the open state as illustrated in FIG. 9.

Next, when operated by the operator, the insertion portion 74 is moved from the proximal end side toward the distal end side, and the distal end parts of the two clip pieces 24A and 24B in the open state are pressed against a treatment part.

Next, in the state in which the distal end parts of the two clip pieces 24A and 24B in the open state are pressed against the treatment part, when the operator operates the operation portion of the treatment tool body 14, the operation wire 78 is moved from the distal end side toward the proximal end side.

Figure 10:
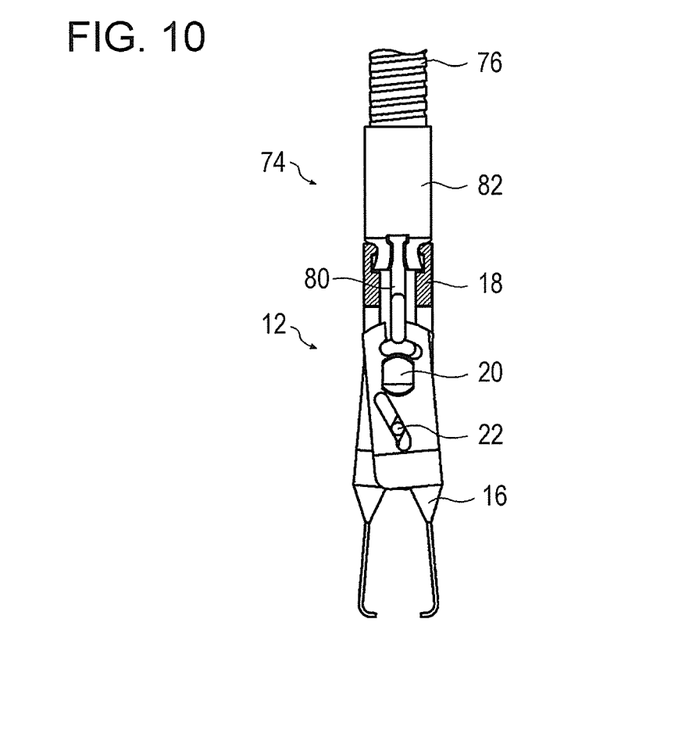
FIG. 10 is an external partial side view of the clip treatment tool according to the present invention, in a state in which the arm portions of the two clip pieces are entering a closed state from the open state.

In accordance with movement of the operation wire 78 from the distal end side toward the proximal end side, the coupling member 80 and the clip body 16 move from the distal end side toward the proximal end side. In accordance with movement of the clip body 16 from the distal end side toward the proximal end side, as illustrated in FIG. 10, the body portions 26 of the two clip pieces 24A and 24B move in such a way that the position of the fixing pin 22 moves along the proximal-end-side regions of the movement holes 32 of the two clip pieces 24A and 24B relatively from the proximal end side toward the distal end side, and the arm portions 28 of the two clip pieces 24A and 24B gradually close from the open state.

In the state before the clip body 16 is locked to the container tube 18, the arm portions 28 of the two clip pieces 24A and 24B can be opened and closed.

That is, in accordance with movement of the coupling member 80 and the clip body 16 from the distal end side toward the proximal end side, the body portions 26 of the two clip pieces 24A and 24B move in such a way that the position of the fixing pin 22 moves along the proximal-end-side regions of the movement holes 32 of the two clip pieces 24A and 24B relatively from the proximal end side toward the distal end side, and the arm portions 28 of the two clip pieces 24A and 24B gradually close from the open state (fully open state) and finally enter the closed state (fully closed state).

When the arm portions 28 of the two clip pieces 24A and 24B gradually close from the open state, the body portions 26 excluding the base portions 36 are contained in the first holes 48A of the container tube 18 from the outside, and the base portions 36 are contained in the second holes 48B of the container tube 18 from the outside. Moreover, when the arm portions 28 of the two clip pieces 24A and 24B gradually close from the open state, overlap between the passage openings 34A of the coupling holes 34 of the two clip pieces 24A and 24B gradually increases, and the opening diameter of the passage openings 34A increases.

When the arm portions 28 of the two clip pieces 24A and 24B enter the closed state, the entireties of the body portions 26 excluding the base portions 36 are contained in the first holes 48A of the container tube 18, and the entireties of the base portions 36 are contained in the second holes 48B of the container tube 18. That is, the body portions 26 of the two clip pieces 24A and 24B are contained in the container tube 18.

On the other hand, in accordance with movement of the coupling member 80 and the clip body 16 from the proximal end side toward the distal end side, the body portions 26 of the two clip pieces 24A and 24B move in such a way that the position of the fixing pin 22 moves along the proximal-end side regions of the movement holes 32 of the two clip pieces 24A and 24B relatively from the distal end side toward the proximal end side, and the arm portions 28 of the two clip pieces 24A and 24B gradually open from the closed state and finally enter the open state.

When the arm portions 28 of the two clip pieces 24A and 24B gradually open from the closed state, parts of the body portions 26 are exposed from the inside of the holes 48 of the container tube 18. When the arm portions 28 of the two clip pieces 24A and 24B gradually open from the closed state, overlap between the passage openings 34A of the coupling holes 34 of the two clip pieces 24A and 24B gradually decreases, and the opening diameter decreases.

When the arm portions 28 of the two clip pieces 24A and 24B enter the open state, parts of the body portions 26 are exposed from the inside of the holes 48 of the container tube 18 to the outside.

Thus, in the state before the clip body 16 is locked to the container tube 18, it is possible to hold a treatment part over again by using the first claw portion 38A and the second claw portion 38B of the two clip pieces 24A and 24B by opening and closing the arm portions 28 of the two clip pieces 24A and 24B. Therefore, it is possible to hold a target treatment part accurately.

Next, in the state in which the treatment part is held by the first claw portion 38A and the second claw portion 38B of the two clip pieces 24A and 24B, the operation wire 78 is moved further from the distal end side toward the proximal end side.

Accordingly, the coupling member 80 and the clip body 16 move further from the distal end side toward the proximal end side, the body portions 26 of the two clip pieces 24A and 24B move in such a way that the position of the fixing pin 22 moves relatively from the proximal-end side regions to the distal-end side regions of the movement holes 32 of the two clip pieces 24A and 24B, and the arm portions 28 of the two clip pieces 24A and 24B enter the closed state. When the arm portions 28 of the two clip pieces 24A and 24B enter the closed state, the passage openings 34A of the coupling holes 34 of the two clip pieces 24A and 24B completely overlap, and the opening diameter becomes the maximum.

Next, the operation wire 78 is moved further from the distal end side toward the proximal end side, while the two clip pieces 24A and 24B are in the closed state.

Accordingly, the coupling member 80 and the clip body 16 move further from the distal end side toward the proximal end side, the body portions 26 of the two clip pieces 24A and 24B move in such a way that the position of the fixing pin 22 relatively moves to the most distal end parts of the distal-end side regions of the movement holes 32 of the two clip pieces 24A and 24B, and the first fitting portion 62A and the second fitting portion 62B of the stopper 20 are respectively fitted into and latched to the first opening 50A and the second opening 50B of the container tube 18.

To be more specific, the body portions 26 of the two clip pieces 24A and 24B move in such a way that the position of the fixing pin 22 relatively moves to the most distal end parts of the distal-end side regions of the movement holes 32 of the two clip pieces 24A and 24B, the first fitting portion 62A and the second fitting portion 62B respectively move to the positions of the first opening 50A and the second opening 50B of the container tube 18, the first stopper member 54 and the second stopper member 56 are urged by the two plate springs 70A and 70B in directions away from each other, and the first fitting member 64A of the first fitting portion 62A and the first fitting member 64B of the second fitting portion 62B are respectively fitted into the first opening 50A and the second opening 50B. Thus, the outer surfaces of the first fitting members 64A and 64B are exposed to the outside of the container tube 18.

When the first fitting members 64A and 64B are respectively fitted into the first opening 50A and the second opening 50B, the outer surfaces of the second fitting members 66A and 66B are in contact with the inner wall surface of the container tube 18. That is, when the first fitting members 64A and 64B are respectively fitted into the first opening 50A and the second opening 50B, the second fitting members 66A and 66B function to prevent the first stopper member 54 and the second stopper member 56 from springing to the outside of the container tube 18.

Thus, the clip body 16 is locked to the container tube 18 while the two clip pieces 24A and 24B are in the closed state, and a treatment part is ligated by the first claw portion 38A and the second claw portion 38B of the arm portions 28 of the two clip pieces 24A and 24B.

Next, in the state in which the clip body 16 is locked to the container tube 18, that is, in the state in which the treatment part is ligated by the first claw portion 38A and the second claw portion 38B of the two clip pieces 24A and 24B, the operation wire 78 is moved further from the distal end side toward the proximal end side.

Accordingly, the coupling member 80 is moved further from the distal end side toward the proximal end side; and, in accordance with movement of the coupling member 80 from the distal end side toward the proximal end side, the hook-shaped distal end part of the latch portion 86 of the coupling member 80 elastically deforms by being pressed by both side surfaces in the width direction of the passage openings 34A of the coupling holes 34 of the two clip pieces 20A and 20B, and is removed through the passage openings 34A. Thus, the two clip pieces 20A and 20B and the coupling member 80 are unlatched from each other, and the clip body 16 and the operation wire 78 are separated from each other.

Figure 11:
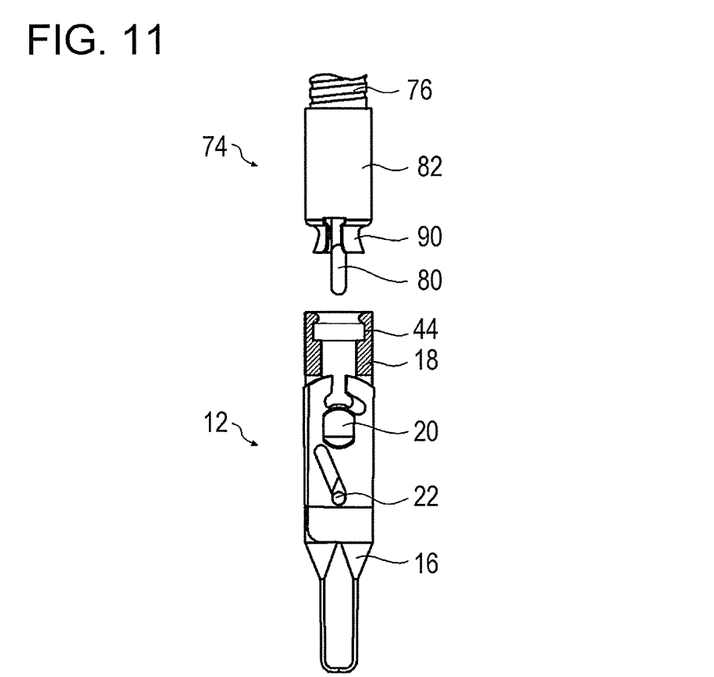
FIG. 11 is an external partial side view of the clip treatment tool according to the present invention, in a state in which a clip unit and the container tube holder are separated from each other.

Next, in accordance with movement of the coupling member 80 from the distal end side toward the proximal end side, a distal end part of the coupling member body 84 moves to a position on the proximal end side relative to the position between the extending portions 94 and the claw portions 96 of the three holding members 92A, 92B, and 92C, the extending portions 94 move closer to each other due to an elastic force, the claw portions 96 of the three holding members 92A, 92B, and 92C and the recessed portion 44 of the container tube 18 are disengaged from each other, and the container tube 18 and the container tube holder 82 are separated from each other. Thus, in the state in which a treatment part is ligated by the clip unit 12, the clip unit 12 is placed at the treatment part.

Subsequently, when operated by the operator, in the state in which the insertion portion 74 of the treatment tool body 14 is still inserted into an endoscope, the insertion portion of the endoscope is pulled out from the inside of the body of the patient. To ligate a plurality of treatment parts, the action described above is repeatedly performed.

Next, actions that are performed to remove the clip unit 12 from a treatment part will be described.

Figure 12:
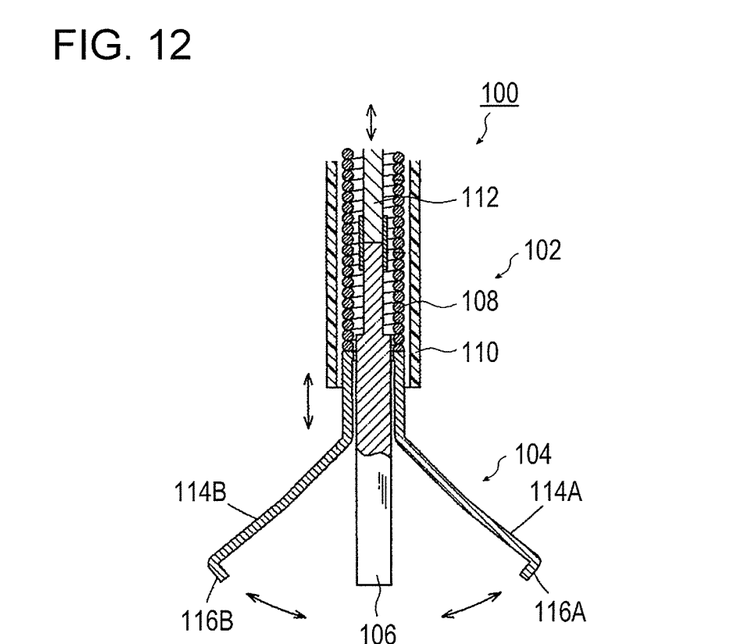
FIG. 12 is a partial sectional view of a clip removing device according to the embodiment.

FIG. 12 is a partial sectional view of a clip removing device according to an embodiment. When operated by an operator, a clip removing device 100 illustrated in FIG. 12 is inserted, for example, from a treatment tool inlet of an operation portion of an endoscope, is extruded from a treatment tool outlet formed in a distal end surface of the insertion portion of the endoscope inserted into the body of a patient, and unlocks the clip unit 12 placed at a treatment part.

The clip removing device 100 has an insertion portion 102, a grasping portion 104, a pushing portion 106, and an operation portion (not shown).

The insertion portion 102 includes a coil sheath 108, a tube sheath 110, and an operation wire 112.

The coil sheath 108 and the tube sheath 110 are flexible tubes that are made of, for example, a fluorocarbon resin such as polytetrafluoroethylene (PTFE) or a resin material such as high-density polyethylene (HDPE).

The coil sheath 108 is inserted through the inside of the tube sheath 110 so as to be movable in the axial direction of the tube sheath 110.

The operation wire 112 is made from, for example, a single wire or a stranded wire made of a metal. The operation wire 112 is inserted through the inside of the coil sheath 108 so as to be movable in the axial direction of the coil sheath 108.

When the operator operates the operation portion of the clip removing device 100, the operation wire 112 moves in the coil sheath 108 toward the distal end side or the proximal end side. That is, the operator can push the operation wire 112 from the proximal end side toward the distal end side or pull the operation wire 112 from the distal end side toward the proximal end side.

The grasping portion 104 has two grasping arms 114A and 114B.

The two grasping arms 114A and 114B are fixed to a distal end part of the coil sheath 108 so as to face each other, and extend so as to become farther from each other from the proximal end side toward the distal end side in a state in which an external force is not applied. The two grasping arms 114A and 114B respectively have claw portions 116A and 116B formed at distal end parts thereof. The claw portions 116A and 116B of the two grasping arms 114A and 114B are portions that clamp and press both end parts of the first stopper member 54 and the second stopper member 56. The claw portions 116A and 116B are respectively formed by bending the distal end parts of the two grasping arms 114A and 114B in directions toward each other.

In accordance with movement of the coil sheath 108 toward the distal end side or the proximal end side, the two grasping arms 114A and 114B can be opened and closed.

That is, in accordance with movement of the coil sheath 108 from the distal end side toward the proximal end side, the two grasping arms 114A and 114B move from the distal end side toward the proximal end side, the two grasping arms 114A and 114B are pressed by an end part of the tube sheath 110 on the proximal end side in directions toward each other and elastically deform, and the two grasping arms 114A and 114B gradually close from an open state (fully open state) and finally enter a closed state (fully closed state).

On the other hand, in accordance with movement of the coil sheath 108 from the proximal end side toward the distal end side, the two grasping arms 114A and 114B move from the proximal end side toward the distal end side, the two grasping arms 114A and 114B gradually open from the closed state due to an elastic force, and finally enter the open state.

The pushing portion 106 is cylindrical and is fixed to a distal end part of the operation wire 112. The outside diameter of the pushing portion 106 is smaller than the inside diameter of each of the coil sheath 108 and the container tube 18.

In accordance with movement of the operation wire 112 from the proximal end side toward the distal end side, the pushing portion 106 moves from the proximal end side toward the distal end side, and a distal end part of the pushing portion 106 pushes the proximal end part of the clip body 16 out of the container tube 18.

The grasping portion 104 and the pushing portion 106 are made of, for example, a material such as stainless steel, titanium, or a cobalt-chrome alloy.

To remove the clip unit 12, first, when operated by the operator, the insertion portion 102 of the clip removing device 100 is inserted from a treatment tool inlet of an endoscope, and the distal end part of the insertion portion 102 of the clip removing device 100, to be more specific, the grasping portion 104 and the pushing portion 106 at a distal end part of the clip removing device 100 are extruded from a treatment tool outlet of the endoscope.

Next, in the state in which the container tube 18 and the container tube holder 82 are separated from each other, that is, in the state in which the clip unit 12 ligates a treatment part and is placed at the treatment part, when the operator operates the operation portion of the clip removing device 100, the two grasping arms 114A and 114B of the grasping portion 104 of the clip removing device 100 are caused to enter the open state.

Figure 13A:
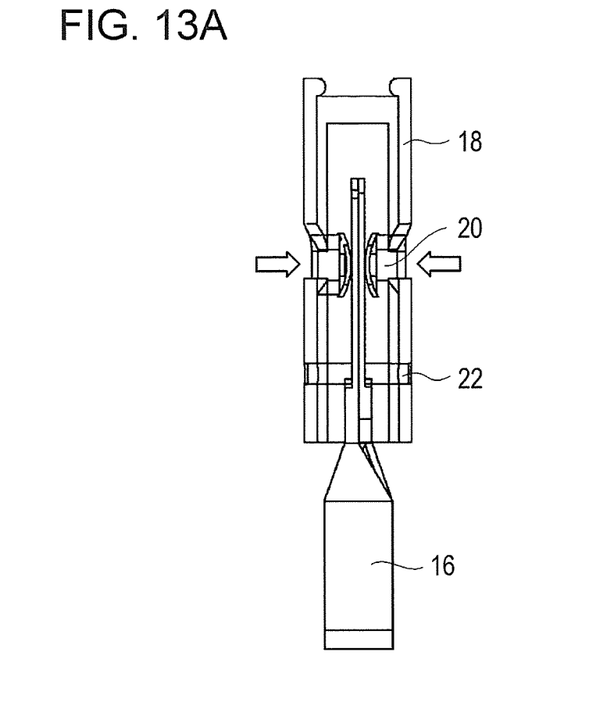
FIG. 13A is an external partial side view of the clip unit, in a state in which the arm portions of the two clip pieces are in the closed state.
Figure 13B:
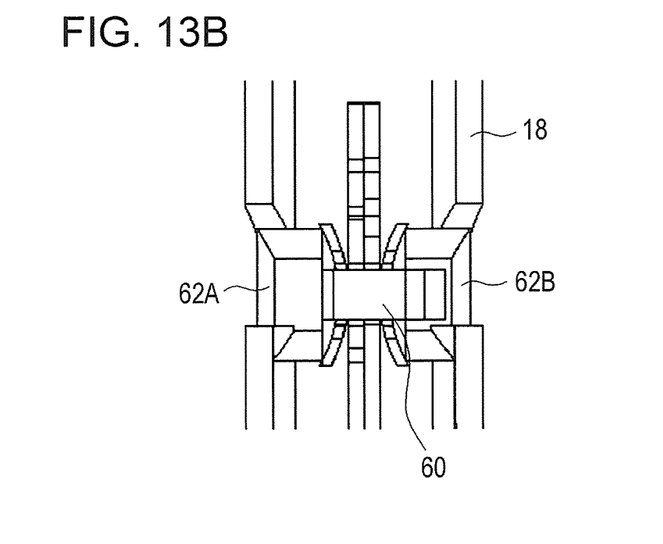
FIG. 13B is an enlarged sectional view of a region near the stopper illustrated in FIG. 13A.

Next, the two grasping arms 114A and 114B of the grasping portion 104 in the open state are gradually closed. As illustrated in FIGS. 13A and 13B, both end parts of the first stopper member 54 and the second stopper member 56 of the stopper 20, that is, the outer surfaces of the first fitting portion 62A and the second fitting portion 62B of the stopper 20 are clamped and pressed from both sides in the axial direction of the through pin 60 by the claw portions 116A and 116B of the two grasping arms 114A and 114B of the grasping portion 104. Thus, the first fitting portion 62A and the second fitting portion 62B of the stopper 20 are respectively released from the first opening 50A and the second opening 50B of the container tube 18, and the clip body 16 and the container tube 18 are unlocked.

To be more specific, both end parts of the first stopper member 54 and the second stopper member 56 are pressed by the claw portions 116A and 116B of the two grasping arms 114A and 114B of the grasping portion 104, the two plate springs 70A and 70B are compressed and elastically deform, and the first stopper member 54 and the second stopper member 56 move closer to each other. The outer surfaces of the first fitting members 64A and 64B move to the positions of the inner peripheral surface of the container tube 18, the first fitting portion 62A and the second fitting portion 62B are respectively released from the first opening 50A and the second opening 50B of the container tube 18, and the clip body 16 and the container tube 18 are unlocked.

Next, in the state in which the clip body 16 and the container tube 18 are unlocked, when the operator operates the operation portion of the clip removing device 100, the operation wire 112 is moved from the proximal end side toward the distal end side.

Figure 14A:
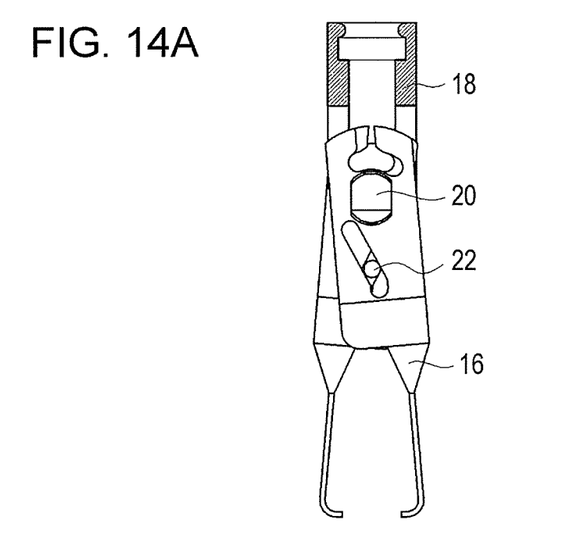
FIG. 14A is an external partial side view of the clip unit, in a state in which the clip body and the container tube are unlocked.
Figure 14B:
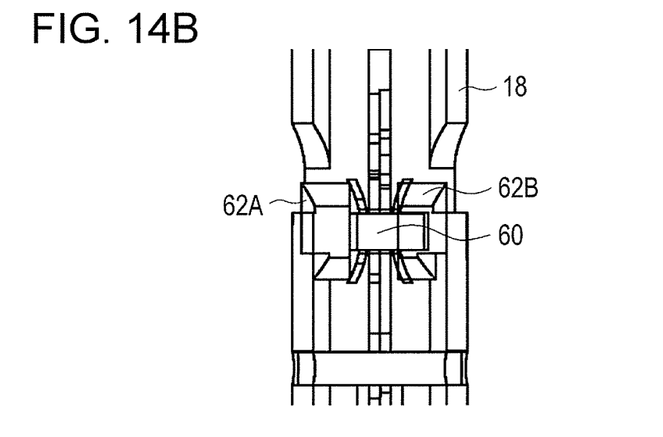
FIG. 14B is an enlarged sectional view of a region near the stopper illustrated in FIG. 14A.

Accordingly, the pushing portion 106 of the clip removing device 100 moves from the proximal end side toward the distal end side, and the distal end part of the pushing portion 106 contacts the proximal end part of the clip body 16. In accordance with further movement of the pushing portion 106 from the proximal end side toward the distal end side, as illustrated in FIGS. 14A and 14B, the proximal end part of the clip body 16 is pushed by the pushing portion 106 toward the distal end side.

Figure 15:
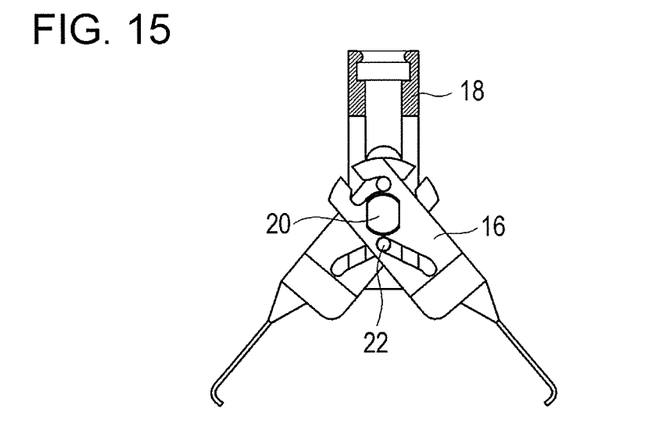
FIG. 15 is an external partial side view of the clip unit, in a state in which the arm portions of the two clip pieces are returned to the open state.

In accordance with movement of the clip body 16 from the proximal end side toward the distal end side, the stopper 20 moves from the proximal end side toward the distal end side, the body portions 26 of the two clip pieces 24A and 24B move in such a way that the position of the fixing pin 22 moves along the movement holes 32 of the two clip pieces 24A and 24B relatively from the distal end side toward the proximal end side, and the arm portions 28 of the two clip pieces 24A and 24B gradually open from the closed state and finally enter the open state as illustrated in FIG. 15. Thus, the clip unit 12 is removed from the treatment part.

Subsequently, when operated by the operator, in the state in which the insertion portion 102 of the clip removing device 100 is still inserted into the endoscope, the insertion portion of the endoscope is pulled out from the inside of the body of the patient. For example, in the state in which both end parts of the first stopper member 54 and the second stopper member 56 are clamped by the grasping portion 104 of the clip removing device 100, the insertion portion of the endoscope is pulled out from the inside of the body of the patient, and the clip unit 12, which has been removed from the treatment part, is also taken to the outside of the body of the patient at the same time. To remove a plurality of clip units 12 from treatment parts, the action described above is repeatedly performed.

With the clip treatment tool 10, until a treatment part is ligated by the clip unit 12, it is possible to hold the treatment part over again by using the two clip pieces 24A and 24B; and, after the treatment part has been ligated by the clip unit 12, because the clip body 16 and the container tube 18 are locked, it is possible to reliably maintain the state in which the treatment part is ligated by the clip unit 12. Moreover, after the clip unit 12 is placed at the treatment part, it is possible to remove the clip unit 12 from the treatment part by unlocking the clip body 16 and the container tube 18 at any desirable timing.

The shapes of the first opening 50A and the second opening 50B of the container tube 18 and the first fitting member 64A and the second fitting member 66B of the stopper 20 are not limited to substantially D-shapes. The shapes are not limited, as long as the container tube 18 and the stopper 20 can be fitted to each other. Only one opening may be formed in the container tube 18 and only one of the stopper members of the stopper 20 may have a fitting member, and the opening of the container tube 18 and the fitting member of the stopper 20 may be fitted to each other.

The shape of the distal end part of the latch portion 86 of the coupling member 80 is not limited to a hook-like shape. The shape of the distal end part is not limited, as long as it is possible to latch the coupling holes 34 of the two clip pieces 24A and 24B and the latch portion 86 to each other.

The holding portion 90 of the container tube holder 82 is not limited to two or more holding members. The structure of the holding portion is not limited, as long as the container tube 18 can be removably attached to a distal end part of the container tube holder 82.

Heretofore, the present invention has been described in detail. The present invention is not limited to the embodiment described above, and naturally, various improvements and modifications are possible within the spirit and scope of the present invention.

REFERENCE SIGNS LIST

10 clip treatment tool
12 clip unit
14 treatment tool body
16 clip body
18 container tube
20 stopper
22 fixing pin
24A first clip piece
24B second clip piece
26 body portion
28 arm portion
30 fixing hole
32 movement hole
34 coupling hole
34A passage opening
36 base portion
38A first claw portion
38B second claw portion
40 container tube body
42 containing portion
44, 68 recessed portion
46A first containing member
46B second containing member
48 hole
48A first hole
48B second hole
50A first opening
50B second opening
52A first insertion hole
52B second insertion hole
60 through pin
62A first fitting portion
62B second fitting portion
64A, 64B first fitting member
66A, 66B second fitting member
70A, 70B plate spring
72 through-hole
74, 102 insertion portion
76, 108 coil sheath
78, 112 operation wire
80 coupling member
82 container tube holder
84 coupling member body
86 latch portion
88 holder body
90 holding portion
92A, 92B, 92C holding member
94 extending portion
96 claw portion
100 clip removing device
104 grasping portion
106 pushing portion
110 tube sheath
114A, 114B grasping arm
116A, 116B claw portion

What is claimed is:

1. A clip treatment tool comprising:
    a clip body that has two clip pieces, each of the two clip pieces having a body portion and an arm portion, the arm portions of the two clip pieces facing each other and respectively extending from the body portions toward a distal end side, each of the body portions of the two clip pieces having a fixing hole formed on a proximal end side and a movement hole formed on the distal end side relative to the fixing hole, the movement hole extending so as to be inclined from a side part in a width direction of the body portion on the proximal end side toward a middle in the width direction of the body portion on the distal end side;
    a container tube that contains the body portions of the two clip pieces therein;
    a stopper that extends through the fixing holes of the two clip pieces and that is attached to the clip body; and
    a fixing pin that extends through the movement holes of the two clip pieces and whose both end portions are fixed to positions in the container tube that face each other,
    wherein the movement hole of each of the two clip pieces has a proximal-end-side region and a distal-end-side region, the proximal-end-side region extending so as to be inclined from the side part in the width direction of the body portion on the proximal end side toward the middle in the width direction of the body portion on the distal end side, the distal-end-side region being located at the middle in the width direction of the body portion on the distal end side and extending from the proximal-end-side region toward the distal end side,
    wherein the arm portions of the two clip pieces open, in accordance with movement of the clip body from the proximal end side toward the distal end side, the body portions of the two clip pieces move in such a way that a position of the fixing pin moves along the proximal-end-side regions of the movement holes of the two clip pieces relatively from the distal end side toward the proximal end side, and the arm portions of the two clip pieces close, in accordance with movement of the clip body from the distal end side toward the proximal end side, the body portions of the two clip pieces move in such a way that the position of the fixing pin moves from the proximal-end-side regions to the distal-end-side regions of the movement holes of the two clip pieces along the proximal-end-side regions of the movement holes of the two clip pieces relatively from the proximal end side toward the distal end side,
    wherein an opening is formed in the container tube, and
    wherein, in accordance with movement of the clip body from the distal end side toward the proximal end side, the stopper moves to a position of the opening and is fitted into the opening, and the clip body is locked to the container tube.

2. The clip treatment tool according to claim 1,
    wherein the position of the fixing pin relatively moves to most distal end parts of the distal-end-side regions of the movement holes of the two clip pieces, and the clip body is locked to the container tube while the arm portions of the two clip pieces are in the closed state.

3. The clip treatment tool according to claim 2, comprising:

a coupling member that has a latch portion on the distal end side, the latch portion being removably latched to proximal end sides of the body portions of the two clip pieces of the clip body and a distal end part of an operation wire being fixed to a proximal end side of the coupling member, the coupling member coupling the clip body and the operation wire to each other, wherein each of the two clip pieces has a coupling hole that is formed in the body portion on the proximal end side of the fixing hole, that extends in the width direction of the body portion, and that is latched by the latch portion, and the coupling hole has a passage opening that is open toward the proximal end side, wherein the arm portions of the two clip pieces gradually close from an open state, overlap between the passage openings of the coupling holes of the two clip pieces gradually increases, and an opening diameter of the passage openings increases, and wherein, while the arm portions of the two clip pieces are in the closed state, the clip body is locked to the container tube, the opening diameter of the passage openings of the coupling holes of the two clip pieces becomes maximum, and, in accordance with movement of the coupling member from the distal end side toward the proximal end side, the latch portion is removed through the passage openings, the two clip pieces and the coupling member are unlatched from each other, and the clip body and the operation wire are separated from each other.

4. The clip treatment tool according to claim 3, comprising:

a container tube holder that has a tubular shape and that has a holding portion on the distal end side, wherein the holding portion has two or more holding members that are disposed so as to face each other, and the two or more holding members respectively have extending portions that extend so as to become closer to each other from the proximal end side toward the distal end side and claw portions that extend so as to become farther from each other from distal end parts of the extending portions toward the distal end side, wherein a recessed portion is formed in an inner peripheral surface on the proximal end side of the container tube, wherein the coupling member has a coupling member body between the latch portion and the operation wire, the coupling member body having an outside diameter larger than an inside diameter of the two or more holding members at a position between the extending portions and the claw portions, wherein the coupling member body is inserted through a space between the two or more holding members, the extending portions of the two or more holding members are pushed and expanded by the coupling member body so as to become farther from each other, the claw portions the two or more holding members are latched to the recessed portion of the container tube, and the container tube is removably attached to a distal end part of the container tube holder, and wherein, in accordance with movement of the coupling member from the distal end side toward the proximal end side, a distal end part of the coupling member body moves to a position on the proximal end side relative to the position between the extending portions and the claw portions of the two or more holding members, the extending portions move closer to each other due to an elastic force, the claw portions of the two or more holding members and the recessed portion of the container tube are disengaged from each other, and the container tube and the container tube holder are separated from each other.

5. The clip treatment tool according to claim 4, wherein, in a state in which the container tube and the container tube holder are separated from each other, outer surfaces of the stopper are pressed, the stopper and the opening are released from each other, the clip body and the container tube are unlocked, and, in accordance with movement of the clip body from the proximal end side toward the distal end side, the arm portions of the two clip pieces gradually open from the closed state and enter the open state.

6. The clip treatment tool according to claim 1, comprising:

a coupling member that has a latch portion on the distal end side, the latch portion being removably latched to proximal end sides of the body portions of the two clip pieces of the clip body and a distal end part of an operation wire being fixed to a proximal end side of the coupling member, the coupling member coupling the clip body and the operation wire to each other, wherein each of the two clip pieces has a coupling hole that is formed in the body portion on the proximal end side of the fixing hole, that extends in the width direction of the body portion, and that is latched by the latch portion, and the coupling hole has a passage opening that is open toward the proximal end side, wherein the arm portions of the two clip pieces gradually close from an open state, overlap between the passage openings of the coupling holes of the two clip pieces gradually increases, and an opening diameter of the passage openings increases, and wherein, while the arm portions of the two clip pieces are in the closed state, the clip body is locked to the container tube, the opening diameter of the passage openings of the coupling holes of the two clip pieces becomes maximum, and, in accordance with movement of the coupling member from the distal end side toward the proximal end side, the latch portion is removed through the passage openings, the two clip pieces and the coupling member are unlatched from each other, and the clip body and the operation wire are separated from each other.

7. The clip treatment tool according to claim 6, comprising:

a container tube holder that has a tubular shape and that has a holding portion on the distal end side, wherein the holding portion has two or more holding members that are disposed so as to face each other, and the two or more holding members respectively have extending portions that extend so as to become closer to each other from the proximal end side toward the distal end side and claw portions that extend so as to become farther from each other from distal end parts of the extending portions toward the distal end side, wherein a recessed portion is formed in an inner peripheral surface on the proximal end side of the container tube, wherein the coupling member has a coupling member body between the latch portion and the operation wire, the coupling member body having an outside diameter larger than an inside diameter of the two or more holding members at a position between the extending portions and the claw portions, wherein the coupling member body is inserted through a space between the two or more holding members, the extending portions of the two or more holding members are pushed and expanded by the coupling member body so as to become farther from each other, the claw portions the two or more holding members are latched to the recessed portion of the container tube, and the container tube is removably attached to a distal end part of the container tube holder, and wherein, in accordance with movement of the coupling member from the distal end side toward the proximal end side, a distal end part of the coupling member body moves to a position on the proximal end side relative to the position between the extending portions and the claw portions of the two or more holding members, the extending portions move closer to each other due to an elastic force, the claw portions of the two or more holding members and the recessed portion of the container tube are disengaged from each other, and the container tube and the container tube holder are separated from each other.

8. The clip treatment tool according to claim 7, wherein, in a state in which the container tube and the container tube holder are separated from each other, outer surfaces of the stopper are pressed, the stopper and the opening are released from each other, the clip body and the container tube are unlocked, and, in accordance with movement of the clip body from the proximal end side toward the distal end side, the arm portions of the two clip pieces gradually open from the closed state and enter the open state.

* * * * *